Figure 1:
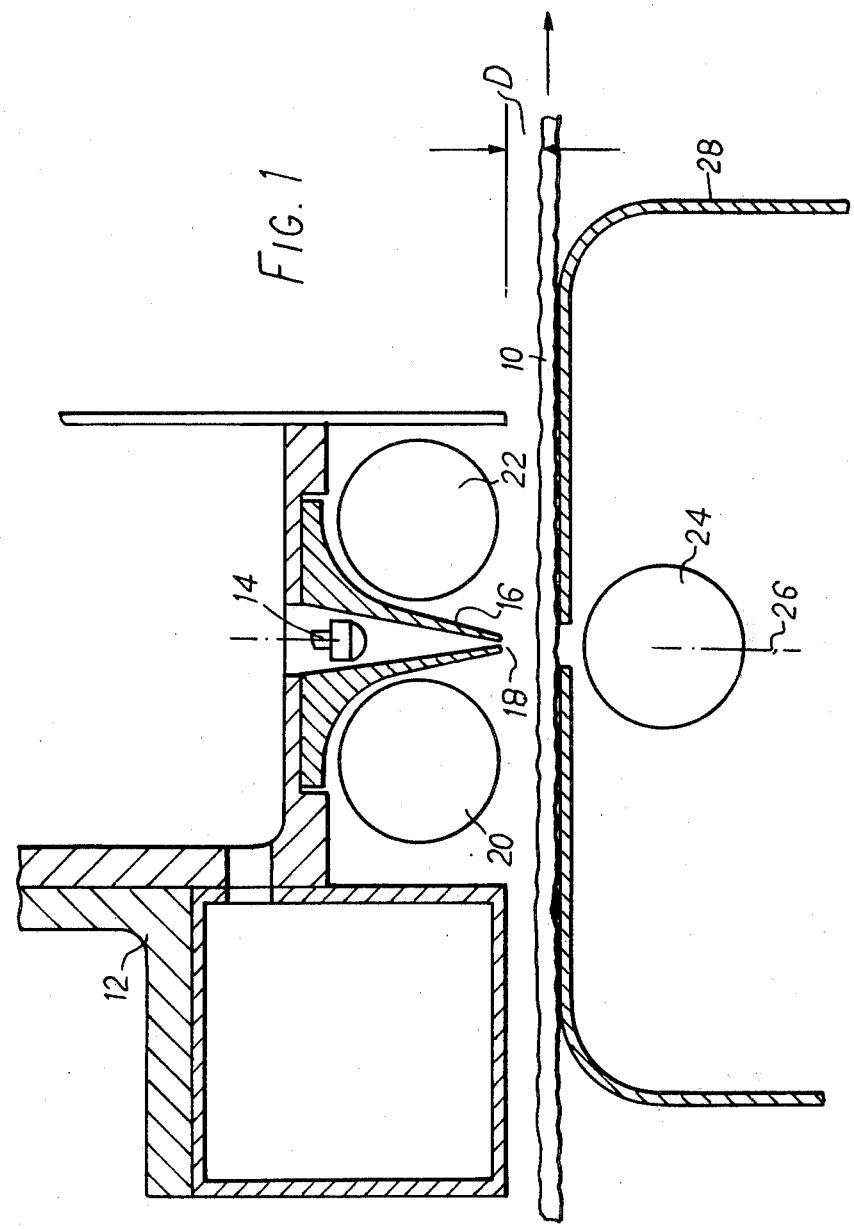

United States Patent [19]

Nash

[11] 4,402,604

[45] Sep. 6, 1983

[54] METHOD FOR THE ON-LINE MEASUREMENT OF INCLUSIONS IN PULP

[76] Inventor: Paul Nash, Kinfauns, Worthing Rd., Horsham, Sussex RH13 7AT, England

[21] Appl. No.: 245,125

[22] Filed: Mar. 18, 1981

[30] Foreign Application Priority Data

Mar. 20, 1980 [GB] United Kingdom ............... 8009464

[51] Int. Cl.³ .................... G01N 21/55; G01N 21/88; G01N 23/12
[52] U.S. Cl. ........................................ 356/237; 162/49
[58] Field of Search ....... 162/198, 263, 262, DIG. 10, 162/49, 238, 258; 356/430, 431, 237, 442; 250/562, 563, 572

[56] References Cited

U.S. PATENT DOCUMENTS

| | | | |
|---|---|---|---|
| 3,827,809 | 8/1974 | Nash | 356/430 |
| 3,833,816 | 9/1974 | Emura et al. | 356/430 |
| 4,093,866 | 6/1978 | Kusdan et al. | 356/431 |
| 4,253,113 | 2/1981 | Decavel et al. | 356/430 |
| 4,255,385 | 9/1981 | Hughes, Jr. et al. | 162/263 |

Primary Examiner—Steve Alvo
Attorney, Agent, or Firm—Kirschstein, Kirschstein, Ottinger & Cobrin

[57] ABSTRACT

Apparatus for inspecting pulp or similar material arranged to flow in a sheet 10 past an inspection station, comprising a row of photosensitive devices 14 arranged to receive light reflected from or transmitted through the material, circuit means 30 receiving the output signals from the photosensitive devices and providing a defect signal when an inclusion in the pulp passes the inspection station, and integrating circuitry 32 adapted to integrate the defect signal with respect to time thereby to measure the total equivalent black area of the sheet 10. To allow for integration over a long travel of the sheet, the integrating circuitry includes an integrator 32, and a pulse generator 34 adapted to receive the output of the integrator and to generate an output pulse when the result of the integration reaches a predetermined magnitude. The integrator is reset to zero on the occurrence of each said pulse, and a counter 36 is arranged to count the pulses generated by the pulse generator.

1 Claim, 5 Drawing Figures

METHOD FOR THE ON-LINE MEASUREMENT OF INCLUSIONS IN PULP

This invention relates to the on-line measurement of dirt in pulp.

Pulp, used for the manufacture of paper, is usually manufactured and sold in the form of pulp board, though sometimes it is manufactured and sold in bulk. The value of pulp, which contains foreign inclusions such as dirt, pitch, and shives (particles of bark), is dependent on its cleanliness. Pulp board is graded according to the degree of contamination in the pulp, which is measured in terms of the equivalent black area (e.b.a.) formed by foreign inclusions in the pulp. For example, a sheet of pulp board having an area of one square meter (i.e. 1,000,000 square millimeters) containing dirt with an e.b.a. of 1 to 5 square millimeters (i.e. 1 to 5 parts in a million) would be graded as good quality board. The same sheet with an average e.b.a. of 30 square millimeters (30 parts in a million) would be second grade material. When the e.b.a. reaches 60 or more parts in a million the material is greatly downgraded in value and is often repulped or rejected.

It is therefore necessary for manufacturers of pulp boards to sample the product frequently by measuring the number and size of foreign particles in single sheets of the board. Due to the high volume output of pulp board machines it is not practical to sample more than one sheet in a thousand, i.e. 0.1% of the output, or even 0.01% on fast machines. This means that only a small fraction of the material in each load, of approximately 1,000 kg, produced by a machine is subject to measurement. Moreover, the need to carry out measurements on single sheets gives rise to a delay in establishing the quality of the board produced.

It is an object of this invention to provide an inspection system which overcomes these disadvantages.

According to this invention there is provided apparatus for inspecting pulp or similar material arranged to flow in a sheet past an inspection station, comprising a plurality of photosensitive devices arranged in a row transverse to the direction of flow of the material so that each device receives light reflected from or transmitted through the material and provides an output signal dependent on the intensity of the reflected or transmitted light, circuit means receiving the output signals from the photosensitive devices and providing a defect signal when an inclusion in the pulp passes the inspection station, and integrating circuitry adapted to integrate the defect signal with respect to time thereby to measure the total equivalent black area per unit of the sheet.

My British Pat. Nos. 885,278, 899,854, 899,855 and 1,437,951 describe apparatus for detecting defects in sheet material flowing past an inspection head, by sensing light reflected from or transmitted through the sheet and impinging on a series of detectors arranged in a line transverse to the direction of flow of the sheet. In the apparatus described in British Pat. No. 1,437,951 (corresponding to U.S. Pat. No. 3,827,809) the light is detected by phototransistors the outputs of which are amplified and then combined through a gating circuit comprising an array of biased rectifiers arranged to reduce the background "noise" level of signals produced by unblemished sheet, and a "defect" signal is produced when the combined output signal exceeds a gate level which is higher than the noise signal. The apparatus also includes circuitry for integrating the combined output signal with respect to time, to detect defects which are narrow in the cross-machine direction and long in the direction of sheet flow. The integrator is reset to zero at predetermined intervals, which in practice correspond to about 10 to 20 millimeters of sheet travel. The described apparatus cannot be used for inspecting pulp because of the need to integrate over several meters of sheet travel.

For example, in a typical pulp board machine the mean web speed is 120 meters/minute, with a web 4 meters wide and having a weight of 208 grams/square meter. The machine thus produces approximately 100 kg of board per minute, cut and slit into approximately 1 square meter size sheets. In 10 minutes the machine produced 1000 kg of board, i.e. a full load in the lay boy, ready for removal. When measured over a time interval such as 10 minutes the random distribution of defects across the 4 meter wide web is uniform, so that, in accordance with a preferred feature of this invention, it is sufficient to use an inspection head monitoring only part of the width of the web, located in any suitable position across the inspection machine, to measure the mean e.b.a. accurately. For example, with a 4 meter wide web the inspection head can be 500 millimeter wide, continuously monitoring 12.5% of the machine output. With such an apparatus, to give an e.b.a. count in square millimeters as parts per million (p.p.m.), inspecting one square meter of sheet area, the pulp board has to travel 2 meters past the inspection head. Assuming a specification of 1 to 5 p.p.m. for first grade and 6 to 60 p.p.m. for second grade pulp, the integrator has to process a wide range, since in 2 meters of travel of the board the total e.b.a. would be in the range 5 to 100 square millimeters, and in 10 meters of board travel the total e.b.a. would be in the range 25 to 500 square millimeters.

In order to enable the accumulated e.b.a. level to be preserved without decay, particularly in apparatus using an analogue integrator, apparatus in a preferred form of the invention employs frequent sampling. The apparatus thus has integrating circuitry including an integrator adapted to receive the combined input signal, a pulse generator adapted to receive the output of the integrator and to generate an output pulse when the result of the integration reaches a predetermined magnitude, means for resetting the integrator to its original condition on the occurrence of each said pulse, and a counter arranged to count the pulses generated by the pulse generator.

Instead of an analogue integrator, a digital integrator may be employed, in which the integrated signal is stored without decay.

The invention may also be applied to apparatus for inspecting pulp in the liquid state. Thus, in accordance with a preferred feature of the invention, the apparatus may include a pair of transparent plates defining between them a flow path for liquid pulp so that the pulp forms a sheet at the inspection station, and means for causing the pulp to flow between the plates.

Figure 2:
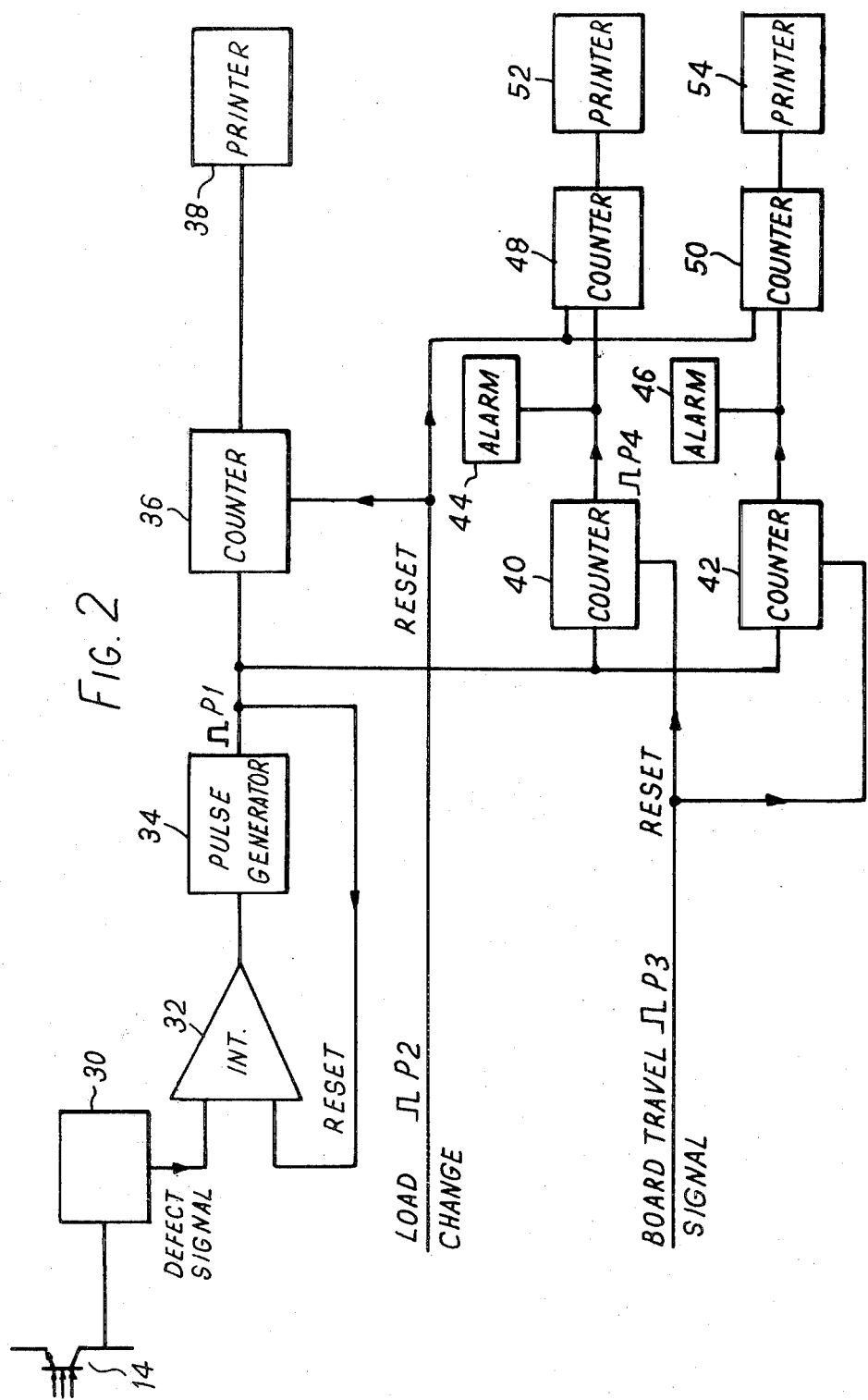
Figure 3:
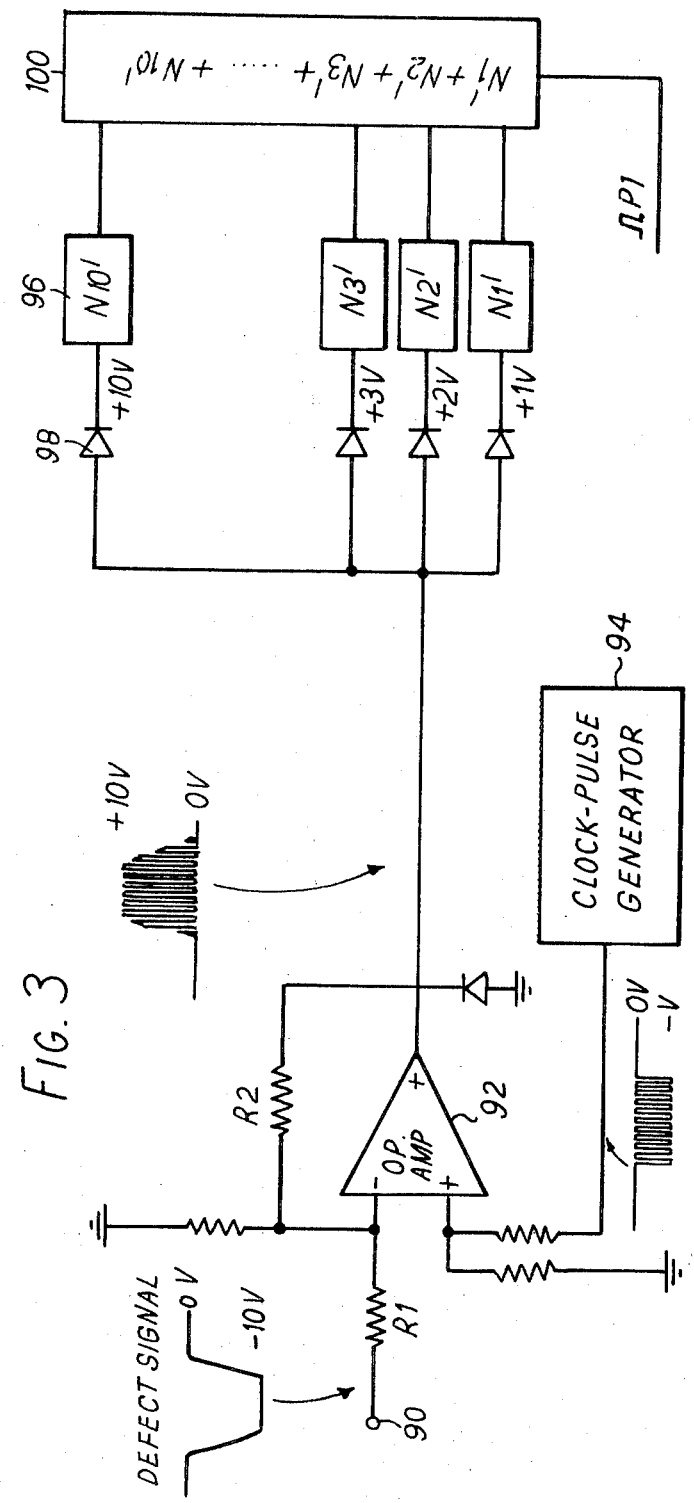
Figure 4:
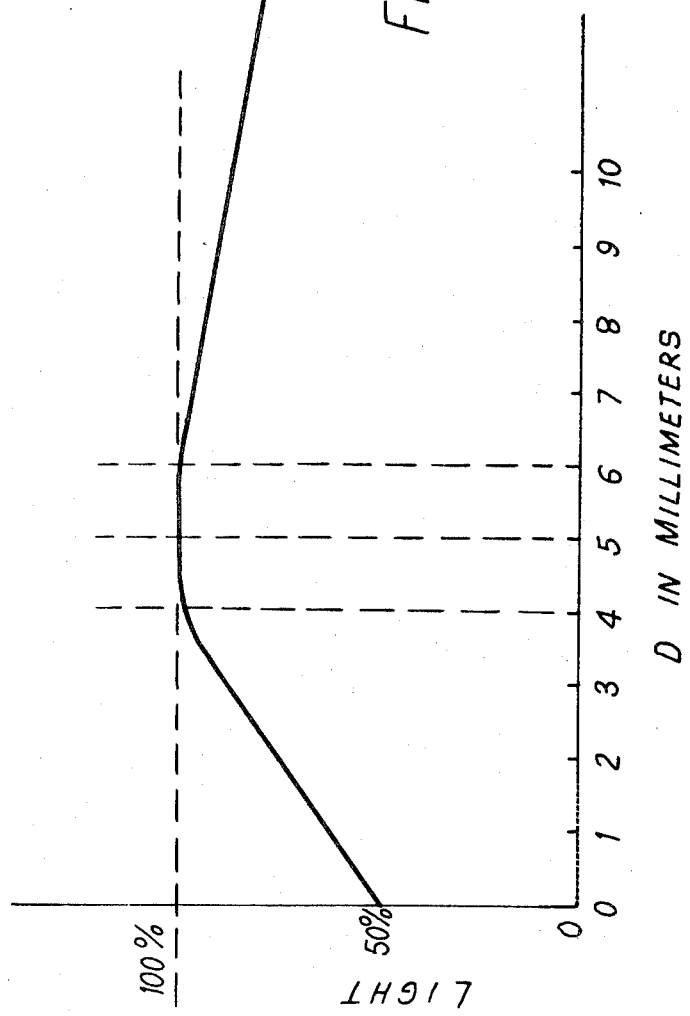
Figure 5:
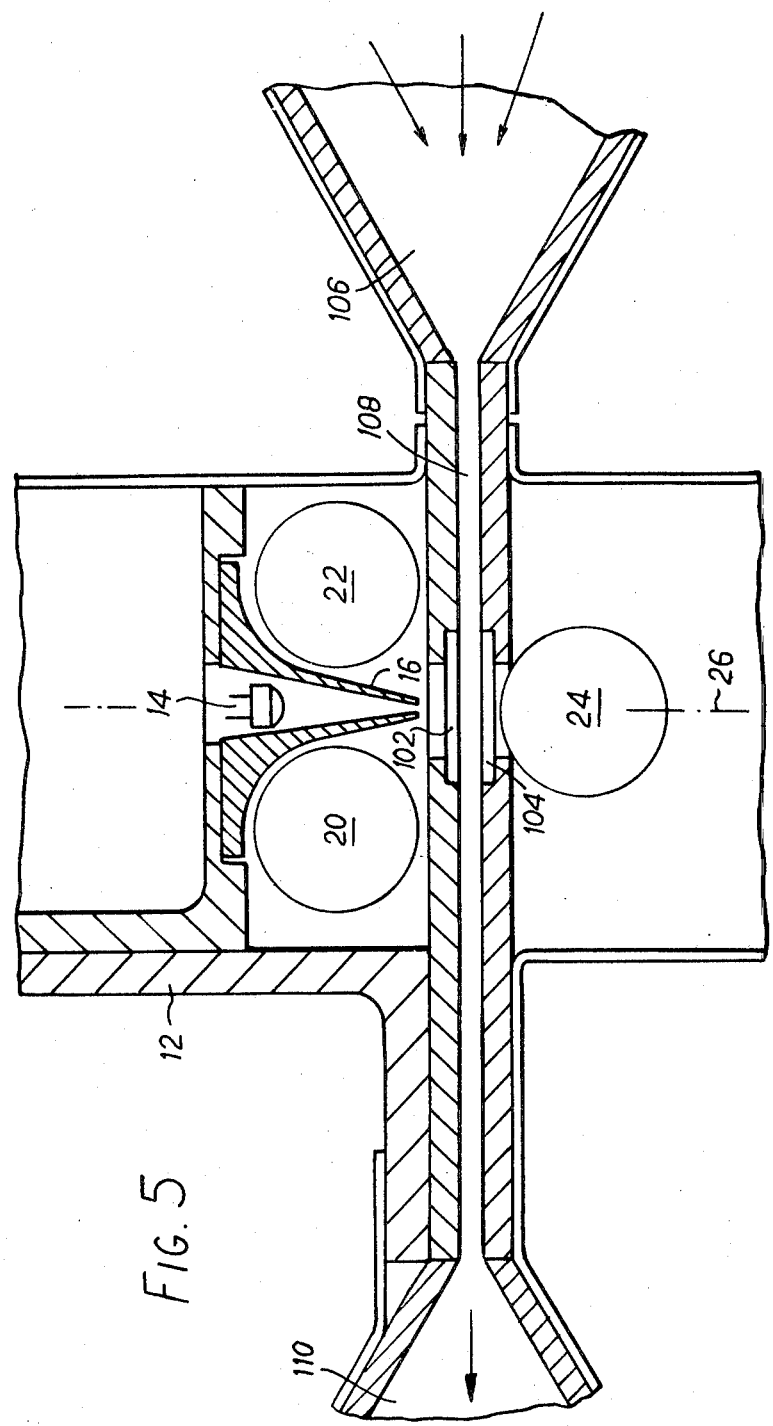

The invention will now be described, by way of example, with reference to the accompanying drawings, in which:

FIG. 1 is a section through an inspection head of apparatus in accordance with the invention for inspecting pulp board, FIG. 2 is a block diagram of electrical circuitry of the apparatus, FIG. 3 is a diagram of digital integration circuitry which may be used in the apparatus, FIG. 4 is a graph illustrating the variation in light sensitivity of photosensors of the apparatus with distance from the inspected material, and FIG. 5 is a section through apparatus in accordance with the invention, modified to inspect liquid pulp.

Referring to FIG. 1 of the drawings, a web 10 of pulp board flows past an inspection head 12 supporting a plurality of phototransistors 14 arranged in a line at right angles to the direction of flow of the pulp board. The head 12 is made up from the requisite number of head units each 130 mm wide and each containing sixteen phototransistors and associated collimating members 16. Each phototransistor views an area of pulp board of approximately 8 mm in width by 0.5 mm, the latter dimension being adjustable. Also mounted on the head 12 are two fluorescent lamps 20 and 22, one on each side of the collimating members 16, and a third fluorescent lamp 24 is positioned beneath the pulp board, in line with the apertures 18 of the collimating members. The lamps 20, 22 and 24, which may be standard one-inch diameter lamps, extend for the required distance across the head, parallel to the row of phototransistors. The head 12 is vertically adjustable, to adjust the separation D between the collimating apertures 18 and the surface of the pulp board 10, and the lower lamp 24 is also vertically adjustable along the optical axis 26.

The pulp board 10 is supported beneath the inspection head 12 on a shoe 28, which has a slit 30, extending beneath the collimating apertures 18, through which light from the lower lamp 24 passes. The shoe is lubricated by dust-free air supplied to a chamber beneath the shoe 28 and escaping through the slit 30. Dust-free air can also be supplied to the head 12 so as to flow over the phototransistors, collimating members and lamps to keep them clean.

The collimating members, and other parts of the inspection head may take various forms as shown in the above mentioned British Pat. No. 1,437,951 and are therefore not described further here.

Referring to FIG. 2, the outputs of the phototransistors 14 are amplified and combined in circuitry 30, which includes an array of diodes forming a gating circuit as described in the above mentioned British Pat. No. 1,437,951, to produce an output signal in which the "noise" signal generated by the unblemished board is much reduced. If the output of a sufficient number, say 50, optical units are so combined the resultant "noise" signal effectively becomes a d.c. signal providing an "internal" gate level in the detection circuitry, so that a signal due to a defect in the pulp board rises above this level this "defect" signal can be amplified to any required level for reliable detection.

The output of the circuitry 30 is supplied to an integrator 32 which integrates the signal with respect to time. The output of integrator 32 is supplied to a pulse generator 34 which produces an output pulse P1 whenever the output of the integrator 32 reaches a preset value corresponding to a predetermined e.b.a. level, of say 25 square millimeters. The output pulse P1 is supplied to the integrator 32 to reset the integrator to zero. The pulse P1 is also supplied to a counter 36. The counter 36 is set to zero by a pulse P2 at the end of each load, and the count N in this displayed or printed out by a printer 38. Multiplying the count N by 25 and by a compensating factor F (described below) and dividing by the number of square meters inspected in each load gives the mean e.b.a. per square meter for the load.

Each output pulse P1 of pulse generator 34 is also supplied to two further counters 40 and 42, each of which is arranged to produce an output pulse (P4 or P5) when the count reaches a preset value. The counters 40 and 42 are reset to zero by a pulse P3 which is generated at the start of each 10 meters of travel of the pulp board past the inspection head, that is once for each inspection of 5 square meters of board. Counter 40 is set to produce a pulse P4 when the count reaches a read-out number N1 which corresponds to the e.b.a. limit for first quality pulp board. For example, if the maximum e.b.a. is 5 square millimeters/square meter, N1 is 25. Whenever the count reaches N1 before the end of the 10 meter sampling distance is reached, a pulse P4 is generated, giving an indication that in the measured 10 meter run the e.b.a. was higher than the set limit. Counter 42 similarly has a preset readout number N2, say 125, corresponding to the e.b.a. limit for second grade pulp board.

The pulses P4 and P5 are supplied to alarm circuits 44 and 46 respectively which actuate audible or visual alarms. The alarms may be bells or buzzers of different pitches or lamps or different colour, so that the two alarms can be easily distinguished.

The pulses P4 and P5 are also fed to fourth and fifth counters 48 and 50, which record how many times in each load the e.b.a. limits were exceeded in the 10 meter sampling distances. Counters 48 and 50 are reset to zero at the start of each load change by the pulses P2, and are connected to respective printers 52 and 54 to produce print-outs of the counts at the end of each load.

The mean e.b.a. for each load is therefore measured by sampling at frequent intervals. Since the integrator 32 is reset whenever the integral reaches a preset value, the actual resetting time will vary. When the quality of the pulp board is exceptionally good the e.b.a. can be as low as one part in a million, and, with the values given above, the resetting interval will then be 25 seconds, that is the time taken for 50 meters of board to pass the inspection head, to reach the resetting level of 25. For poor quality board the resetting interval can be as short as 0.25 seconds.

The decay time of the integrator should be an order of magnitude greater than the longest resetting interval, i.e. 25 seconds. This can be achieved with an analogue integrator, such as that shown in FIG. 15 of the above mentioned British Pat. No. 1,437,951 (in the circuit of FIG. 15 the output signal 232 of the integrator decays according to the time constant of coupling capacitor 224 and resistors 251 and 226 in series. Using good quality, commercially available components it is practical to assume a decay time of 200 seconds—$C_{224} = 100$ microfarads, $R_{251-252} + R_{226} = 2$ megohm, $T = 10^{-4}$ farad $\times 2 \times 10^6$ ohms $= 200$ seconds).

Alternatively, digital means can be used to measure the e.b.a. of pulp, which may conveniently be implanted using a microprocessor or microcomputer. As the shortest defect pulse duration is of the order of 0.4 milliseconds (i.e. a 5 kH$_2$ highest system response is sufficient) a 50 kH$_2$ clock-pulse generator can be used, the shortness defect pulse being then sampled by at least ten digits. A suitable integrator is shown in FIG. 3. The output of circuit 30 is applied through terminal 90 and resistor R1 to the inverting input of operating amplifier 92, the non-inverting input of which receives clock-pulses from generator 94. The analogue signal, caused by detection of a defect, supplied to the amplifier is therefore digitised, the output of the amplifier providing a series of pulses which are supplied to a series of counters 96 through an array of biased diode gates 98. In the example shown, in which the peak defect signal level is 10 volts, the diode array consists of ten diodes, which are subject to respective reverse biasing voltages of 1 volt, 2 volt, and so on up to 10 volts. A pulse of 10 volts is therefore passed by all ten diode gates, and is recorded by all ten counters 96, whilst a pulse of, say, 4 volts is passed only by the first four diode gates and is recorded by four of the counters. The resulting counts $N1'$, $N2'$ ... $N10'$ are summed in a further counter 100, the sum representing the integral of the defect signal applied to terminal 90. As described above, the counter 100 is reset to zero by pulse P1 when a count is reached corresponding to an e.b.a. of 25.

The total integrating time required to reach an e.b.a. of 25 square millimeters (when each inclusion appears full black) is 25 millimeters divided by 2 meters per second (the web speed), i.e. 12.5 milliseconds. Allowing for excess storage in the memory of the microprocessor 25 milliseconds, say, can be adopted as the total integration time during a sampling period. The requisite memory capacity of the microprocessor would then be (with 50 kH$_2$ clock pulses and 10 bits for a pulse of maximum amplitude) $50,000 \times 0.025 \times 10 = 12,500$ bits.

In addition to the reduction in the background "noise" signal by combining signals from a number of photosensors, the "noise" is further reduced in the apparatus of this invention, as will now be described.

The symmetrical illumination from the lamps 20 and 22 in the inspection head 10 much reduces the "shadow effect" caused by corrugation of the surface of the pulp board, and therefore reduces the "noise" signal generated by unblemished board. The effect of surface corrugation can be further reduced or eliminated by selecting the distance D between the collimating apertures 18 and the upper surface of the board to be at its optimal value. When the apertures are very close to the surface of the board little reflected light reaches the photosensors 14. As the apertures are raised more and more reflected light reaches the sensors, until beyond a well-defined distance the light reaching the sensors decreases. FIG. 4 shows a typical light sensitivity curve of the photosensors as a function of the distance D. At the optimum distance, i.e. about 5 millimeters in the case of the particular apparatus giving the curve shown, the light reaching the photosensors 14 is largely unaltered by small changes in the distance D. The "noise" due to surface corrugation is therefore substantially eliminated and the system is not affected by board flutter.

The "noise" due to the "formation" of the pulp board, i.e. irregularities in the consistency and transparency of the board due to the fibrous nature of the pulp, can be eliminated by balancing the light from lamps 20 and 22 and from lamp 24 below the board, so that the board is illuminated equally from above and below.

The location of a defect within the thickness of the board has little effect on the defect signal, as long as the transparency of the board is not too low. A spot on the surface of the board facing the inspection head is seen as it is, namely a small and intense spot. The same defect on the underside of the board is diffused and appears larger and fainter. Since the system integrates the defect signal, to produce a signal proportional to the product of the intensity and area of the defect, the integrated signal amplitude is similar for both locations of the defect. When the light illuminating the board from above and below is balanced, and when the transparency of the board is such that 50% of the incident light is transmitted through the board (as shown by the curve in FIG. 4 when D=0, i.e. when no reflected light reaches the photosensors), the location of a defect within the thickness of the board does not affect the defect signal.

If however the transparency of the board, is typically from 1 to 3 millimeter thick) is low, the integrated defect signal is more attenuated the greater the depth of the inclusion in the board. Since the random distribution of dirt in the board is uniform, taken over a full load, a factor F by which the measured e.b.a. must be multiplied to take this attenuation into account can be determined. The factor F can be determined for any particular thickness and grade of board by using a simple test apparatus. The test apparatus has the same mechanical and optical configuration as the apparatus shown in FIG. 1, except that it is sufficient to use only one optical unit, or a pair of non-adjacent optical units connected to a differential amplifier. A sample board, of say 200 mms by 100 mms, is moved in say 0.1 millimeter steps at right angles to the collimating aperture. Conveniently a 1 square millimeter black spot is attached to the top of the board and several identical spots are attached to the underside at intervals, all the spots being in line in the direction of the movement of the sample. As the spots are moved in 0.1 millimeter steps under the aperture the integrated area of the signal generated by each spot can be measured. The integral of the defect signal S of the spot at the top of the board defines one e.b.a. The attenuation of the integrated signals corresponding to the spots at the underside define the factor F. The signals Su from these spots vary according to the formation of the board. The sum of these signals Su divided by their number define the mean signal Sm.

The factor F can then be calculated by the formula:

$$F = \frac{S}{Sm + \frac{(S - Sm)}{2}}$$

the mean position of an inclusion being within the board at a depth of half its thickness.

The factor F can be calculated using an analogue or digital integrator, or alternatively the signals can be plotted and evaluated graphically. Using the test apparatus, the factor F can be established for boards of different thicknesses and grades as used in a pulp mill.

FIG. 5 illustrates a modified form of the apparatus according to this invention which can be used to inspect pulp in liquid form. It can be used, for example, by a pulp manufacturer to inspect pulp before its final processing to bulk pulp material or by a pulp user, such as a paper mill, to inspect pulp before it reaches the wire of a paper machine.

A fraction of the liquid pulp is diverted to the apparatus, where its e.b.a. is measured as in the first described embodiment. However, instead of a corrugated wet, semi-dry or dry pulp board, a "liquid sheet" of pulp is examined as it is forced past the inspection head 12 between two parallel glass plates 102 and 104 defining an aperture window. The liquid pulp is supplied to the plates through an enclosure 106. The pulp passes through a pump and a flow control valve and is mixed in enclosure 106 with pure liquid, with no fibre content, supplied through a second flow control valve. By this means the pressure and consistency of the mixture in enclosure 106 can be adjusted to satisfy two criteria namely, first to obtain sufficient flow between the plates 102, 104 to give a significant sampling rate for the e.b.a. measurement, and second to do this at a consistency at which the factor F equals 1, that is when the amount of light reflected from and transmitted through the pulp is the same. The pump enclosure 106 is designed to agitate and thoroughly mix the pulp and liquid content along the whole length of the inspection head and aperture window 102, 104, that is in a dimension at right angles to the pulp-flow, and to do so before the pulp reaches the aperture window.

The pulp is returned to its source via an enclosure 110, which may contain a filter for the removal of the excess liquid content so that the consistency of the returned pulp is the same as it was originally.

I claim:

1. A method of inspecting liquid paper pulp flowing past an inspection station, comprising:

(A) providing at the inspection station a pair of transparent plates defining a flow path for the pulp so that the pulp forms a sheet of predetermined thickness at the inspection station,
 (B) positioning light sources on both sides of the sheet,
 (C) arranging a plurality of photosensitive devices on one side of the sheet in a row transverse to the direction of flow of the pulp so that each device receives light reflected from and transmitted through the sheet and provides an output signal dependent on the intensity of the reflected and transmitted light,
 (D) mixing the pulp with liquid having no fibre content to modify its consistency,
 (E) causing the pulp to flow between the plates,
 (F) adjusting the position of the light sources and the thickness and consistency of the sheet of pulp so that the amount of light reflected from the sheet to the photosensitive devices is equal to the amount of light transmitted through the sheet to the photosensitive devices,
 (G) supplying output signals from the photosensitive devices to circuit means which provide a defect signal when an inclusion in the pulp passes the inspection station,
 (H) supplying the defect signals to integrating circuitry which integrates the defect signals with respect to time,
 (I) resetting the integrating circuitry when the integration reaches a preset value, and
 (J) counting the number of times the preset value is reached, thereby to measure the total equivalent black area of the sheet.

* * * * *